United States Patent [19]

King et al.

[11] 4,408,160

[45] Oct. 4, 1983

[54] ACOUSTIC BARKHAUSEN STRESS DETECTOR APPARATUS AND METHOD

[75] Inventors: James D. King; Gary L. Burkhardt; John R. Barton; George A. Matzkanin, all of San Antonio, Tex.

[73] Assignee: Southwest Research Institute, San Antonio, Tex.

[21] Appl. No.: 252,246

[22] Filed: Apr. 8, 1981

[51] Int. Cl.³ .................... G01B 7/24; G01N 27/72; G01R 33/12

[52] U.S. Cl. .................... 324/209; 324/228; 324/235; 324/238; 73/587; 73/779; 73/801; 73/862.36; 73/862.69; 73/DIG. 2

[58] Field of Search ............... 324/209, 228, 235, 237, 324/238; 73/779, 587, 801, DIG. 2, 862.36, 862.69

[56] References Cited

U.S. PATENT DOCUMENTS

| 3,427,872 | 2/1969 | Leep et al. | 324/209 |
| 3,783,370 | 1/1974 | Birdwell et al. | 324/209 |

OTHER PUBLICATIONS

Karjalainen et al, Influence of Tensile and Cyclic Loading Upon Barkhausen Noise in a Mild Steel, Materials Evaluation, Aug. 1979, pp. 45-51.
Ono et al, Magnetomechanical Acoustic Emission of Iron and Steel, Materials Evaluation, Jan. 1980, pp. 55-61.
Ono et al, Magnetomechanical Acoustic Emission for Residual Stress and Prior Strain Determination, Technical Report to the Office of Naval Research, 10/79.
Pasley, Barkhausen Effect-An Indication of Stress, Materials Evaluation, vol. 28, No. 7, Jul. 1970, pp. 157-161.
Sundström et al, The Use of Barkhausen Noise Analysis in Nondestructive Testing, Materials Evaluation, Feb. 1979.

Primary Examiner—Gerard R. Strecker
Assistant Examiner—Warren S. Edmonds
Attorney, Agent, or Firm—Gunn, Lee & Jackson

[57] ABSTRACT

This disclosure is directed to an acoustic Barkhausen stress detector apparatus and a method of obtaining measurements of stress in or determination of the microstructure of ferromagnetic materials. In the preferred and illustrated embodiment, stress or microstructure information in a ferromagnetic specimen is tested and measured through application of a variable magnetic field. A sensitive acoustic detecting device including an input transducer(s) and amplifier(s) forms a signal based on Barkhausen acoustic phenomena which arise from a change in the magnetic field strength. Barkhausen acoustic information is in the form of vibrations produced within the material which occur as magnetic domain walls shift. The domain wall shifts occur at various locations within the material of interest, and the acoustic vibrations are propagated through the material and are observable at the surface by one or more transducers. The transducer and amplifier system forms output signals dependent on the stress levels and influenced by the microstructure in the material. After amplification and display on a suitable recording device, the signals are scaled to relate the stress and microstructure within the specimen. An array of transducers and associated amplifiers enables spatial resolution of stress distribution in a specimen.

28 Claims, 2 Drawing Figures

ACOUSTIC BARKHAUSEN STRESS DETECTOR APPARATUS AND METHOD

BACKGROUND OF THE DISCLOSURE

An observer by the name of Barkhausen identified Barkhausen magnetic domain shift phenomena in about 1917. This phenomena is a transition which occurs within a ferromagnetic specimen during magnetization. The phenomena description postulates that the specimen is formed of innumerable small magnetic domains. A domain is a three-dimensional portion of the specimen, which particular portion is deemed to act as a small magnet initially postured in a randomly oriented position within the specimen. The domains are randomly distributed and positioned when the specimen is in a nonmagnetic state. The three-dimensional integration of the magnetic force formed in bulk by the specimen is nil as a direct result of the random orientation of the various domains within the specimen.

When a magnetic flux is applied to ferromagnetic material, the flux forces reorientation of the domains. Thus, the domains are observed to shift suddenly. The shifting is cumulative, as first one domain and then another shifts as they are aligned with the magnetic flux direction. Shifting and change in domain size occur both separately and together. As an example, one domain may only rotate. Another will expand as its borders (walls) move which expansion will inevitably reduce the volume of adjacent domains. Shifting of domain walls occurs suddenly, accompanied with an acoustic wave and a change in magnetic intensity in the specimen. As the flux increases, the number of domains aligned with the lines of flux increases. Each shift of a domain is accompanied by magnetic perturbation indicative of the shift. So to speak, the shift by the domain is a reorientation of the domain and may be likened to rotation of a small magnet within a ferromagnetic material. When the small magnet is rotated, it induces a changing field in the adjacent ferromagnetic material, and it is possible to measure this phenomena externally. Indeed, the shift phenomena is observed by review of the magnitude of the Barkhausen signal, the signal being the amplitude of the envelope of the distribution of voltage pulses induced during a change in magnetization. This method of detection is called the Barkhausen magnetic effect.

The Barkhausen magnetic effect is stress dependent. Speaking generally, for materials with a positive magnetostrictive coefficient, the activity increases when the specimen is under tension and decreases when the specimen is under compression. Thus, Barkhausen magnetic signal strength is a measure of the nature and magnitude of the stress occurring in the test specimen at the moment of magnetization. The present invention overcomes some limitations of induction-type Barkhausen magnetic test apparatus described in U.S. Pat. No. 3,427,872. Although domain walls located throughout the entire magnetized volume of a specimen undergo movement when the applied magnetic field strength is varied, only those domain wall movements near the surface can be detected inductively since those deeper within the specimen are electromagnetically shielded. So to speak, the signal strength is shielded by the specimen, itself, so that Barkhausen measurements obtained inductively show only surface occurrences, which data is therefore incomplete. In many instances, stress distribution is not necessarily even or uniform. Given a particular specimen, the stress may concentrate in the central portions of material and not manifest itself near the surface. Because inductive detection of Barkhausen phenomena is possible only at the surface, the surface manifestation must inevitably be the only measure available.

The present disclosure is concerned in the main with utilization of the Barkhausen acoustic phenomena for repeatable nondestructive testing of a specimen. It has been discovered that the sudden movement of magnetic domain walls creates a unique vibratory signal which travels through the specimen. The direction of propagation appears to include all possibilities so that domain wall shifts, even those deep within a specimen, produce vibrations which travel to the surface, probably all surfaces. Barkhausen acoustic sounds thus occur with movement of the various domain walls in the specimen. The shifts so occurring are readily detectable at the surface by an acoustic transducer. It has been found that Barkhausen acoustic signal is dependent on residual and applied stress existing in the specimen as well as the characteristic of the microstructure of the specimen. Thus, utilizing appropriate scale factors, the Barkhausen acoustic phenomena will form an indication of the stress level of microstructure in encompassing regions of the specimen extending from the surface to the interior.

BRIEF DESCRIPTION OF THE DISCLOSURE

The present invention is, therefore, summarized as apparatus which tests a specimen undergoing stress in a nondestructive fashion by placing a variable magnetic field on it. As the magnetic field is varied, the specimen is observed by means of an acoustic vibratory wave sensor or transducer. The transducer is connected with suitable amplifier and filter means. The output signal level may be indicated on a meter or an oscilloscope or recorded on a time base recorder which displays data dependent on and a function of existent stress levels within the specimen. By calibration against known specimens, the material undergoing testing can be tested for variations in stress and stress levels, and the test phenomena is repeatable with different specimens of the same type of metal and configuration. Through the use of an array of transducers, each connected to suitable amplifiers, the stress can be mapped spatially to determine the magnitude and direction of applied and residual stress throughout, or at selected locations in the measured region of the tested material.

A method is also disclosed which utilizes the steps of placing a time variant field on a specimen, observing the specimen with an acoustic sensor to pick up the pulses of domain wall shifts measuring, plotting or charting the acoustic signals as a function of time or at selected times relative to the time varying magnetic field and interpreting the data by application of suitable scale factors.

DETAILED DESCRIPTION OF THE DISCLOSURE

Figure 1:
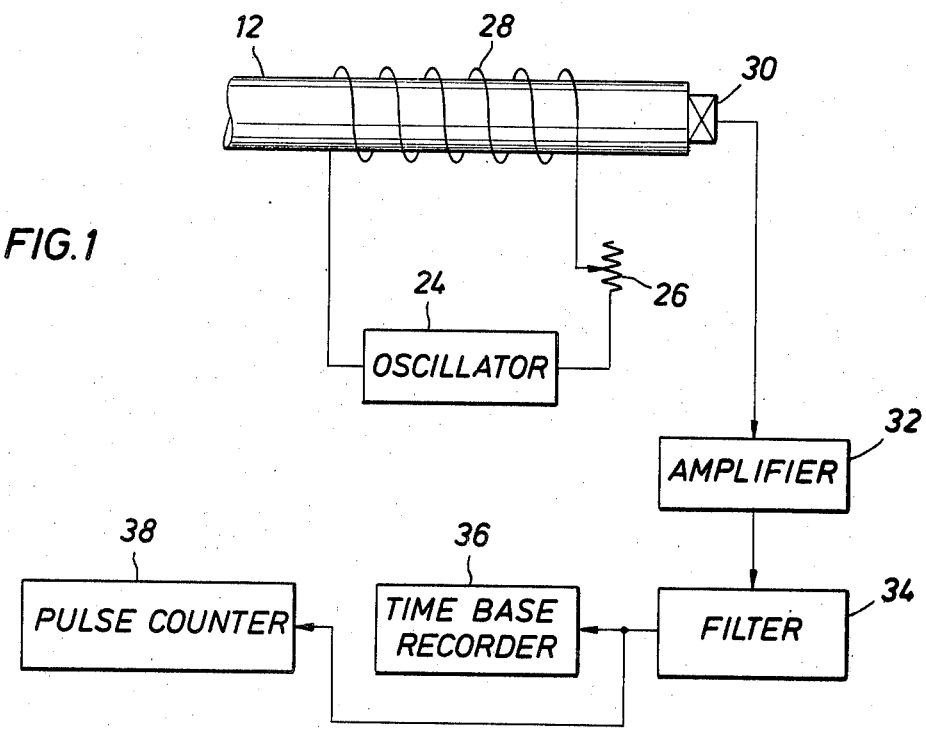
FIG. 1 is a schematic diagram of the present invention disclosing one arrangement for testing a specimen.
Figure 2:
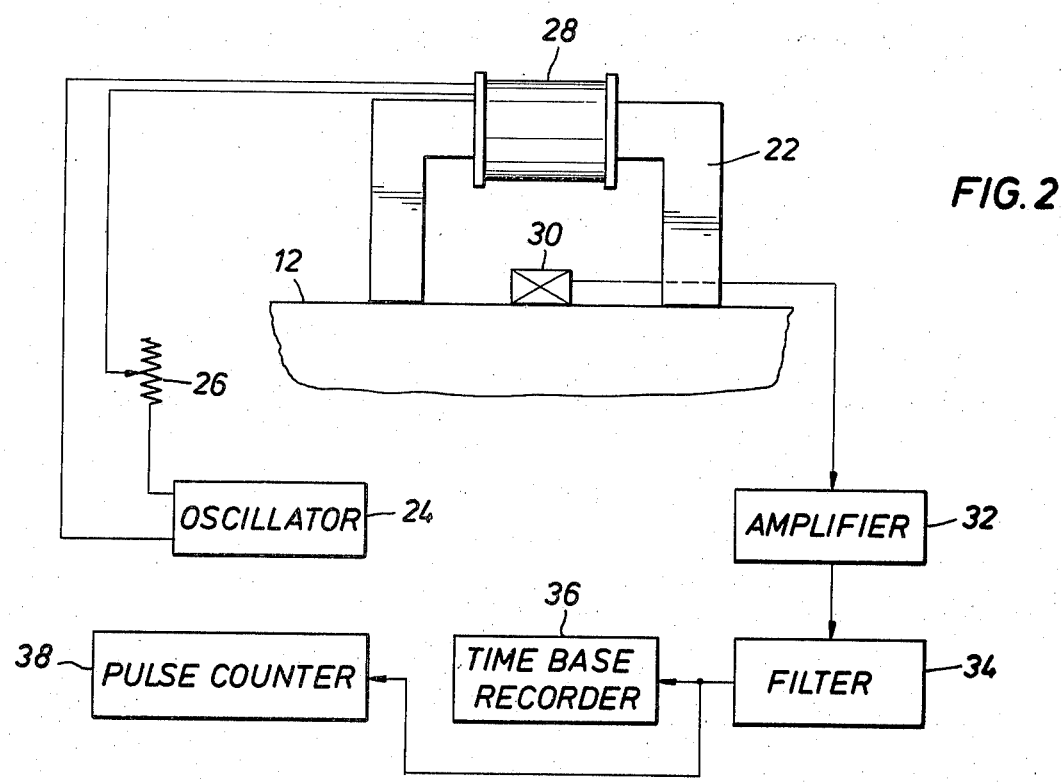
FIG. 2 is an alternate form of test apparatus shown in schematic form for testing another specimen.

FIG. 1 shows test apparatus devised for testing a particular specimen 12 having the shape of a rod. The present invention is able to test specimens of other sizes and shapes; the rod 12 is merely an exemplar of specimen form and shape. Specimen geometry is variable over a wide range. Solid specimens can be tested, as well as those made of relatively thin walls. As examples, H beams, hollow box structures, hollow tubes and various other shapes can also be tested using the test apparatus of FIGS. 1 and 2. The present invention includes an oscillator 24 which forms an output signal of a selected frequency and shape. Signal shape ranges from a sine wave to ramps. The output signal is supplied through a rheostat 26 which controls the signal level of the oscillator. In turn, the signal is applied to a coil 28 which is positioned around the specimen (FIG. 1) or alternatively to a "C" shape electromagnet (including a coil 28 and pole pieces 22) which is placed next to the specimen (FIG. 2). The entire specimen or a selected portion thereof is thus placed within a magnetic field, preferably a time variant field. The field intensity variation can be a ramp, a sinusoid, or of an abrupt and nonlinear shape between an initial value and some maximum. As the field varies, typically from some initial intensity to an increased intensity, the variations are manifested within the specimen by a shift in magnetic domain walls which is accompanied by an acoustic vibration. So to speak, when the domain suddenly moves to a new position due to influence of the magnetic field, domain movement forms an acoustic wave which is transmitted through the specimen. The specimen has relatively good acoustic transmission abilities, and therefore, whether the domain wall is located near the surface or deep within the specimen, an acoustic wave is formed and transmitted through the material.

The acoustic wave formed in the specimen by magnetic domain wall motion is transmitted through the medium of the specimen and impinges on the surface at some location, perhaps on all or most surfaces. An acoustic transducer 30 is placed in contact with, or in proximity to, the specimen, there being no apparent theoretical position or location of the acoustic transducer. Some limits may be practical, namely, accessibility, and other limits may be a matter of symmetry or of reduced intensity as the transducer is located further from the site where the vibrations are initiated or is less strongly coupled to the specimen. Even with an off-center location for the acoustic transducer 30, the Barkhausen acoustic vibration is coupled to the transducer which detects and forms an output signal representative of the Barkhausen magnetic domain wall shifts.

An amplifier 32 is connected to the transducer, and it forms much larger signals. The amplifier is able to provide a significant amount of gain inasmuch as the signals from Barkhausen magnetic domain wall shifts are relatively small. The signal from each domain wall shift is in the form of a sharp pulse which is relatively brief and narrow. The pulse form while not terribly uniform, is of such predictable frequency spectral content and amplitude that it can be detected upon passing through a band pass filter 34 set to pass the signal of interest. Obviously, magnetic domains within the specimen 12 are relatively small and, therefore, quite numerous. Dependent on scale factors, the number of domains measures in the thousands or hundreds of thousands, and, accordingly, the filter 34 is provided with thousands or hundreds of thousands of pulses and rejects signals outside a specified band width.

The present phenomena is dependent on tensile and compressive stress. In certain materials it has been found that, with minimum stress, the number of pulses and pulse amplitude from a given specimen are maximum and decrease with tensile stress. In other words, the pulse count and amplitude in the aggregate is maximum with no stress. The total number of pulses and pulse amplitude decreases with stress in a fashion which is more or less linear. On placing compressive stress on the specimen, the pulse count and amplitude also decreases in a more or less linear fashion.

Returning now to the filter 34, it normally must pass pulses which have a pulse width of approximately 1.0 millisecond or less in a steel specimen. The pulse width obtained from some specimens is in the range of about 10.0 microseconds or less. The signal magnitude obtained from the transducer is in the microvolt range. These, of course, are scale factor dependent on the bulk of the specimen, the coupling between the specimen 12 and the acoustic sensor 30 and other like factors. It is sufficient to note that the width of the pulses resulting from various magnetic domain wall shifts in a given specimen is reasonably predictable within a specified range. The pulse amplitudes also fall within a specified range.

As the pulses occur, they are supplied to a time base recorder 36 or pulse counter 38 which may be used to indicate, chart or plot the pulse amplitudes and/or number of pulses occurring in a given time interval. Other data capture and recording or indicating systems are known, including meters, oscilloscopes, sample and hold amplifiers, spectrum analyzers and the like. The chart or plot is substantially nil with no magnetic flux and also at a constant flux. However, during the change in flux from a given initial level to a specified ending flux value, the pulses are observed and noted, to yield a chart of pulses proportional to the stress in the specimen. It should be noted that for certain materials maximum cumulative pulse count occurs with minimum stress. As the stress increases, it retards or reduces the number of pulses in the aggregate. The area under the curve of pulse rate as a function of magnetic field intensity, as the field is swept over the appropriate range, will provide a sum total representative of the number of pulses. The inverse relationship holds true, the same area under the curve can be related via a scale factor to the stress in the specimen.

The first step in utilizing the present invention is to obtain a calibration or indication of total pulse count and/or pulse amplitude versus stress for a given specimen configuration and grade of metal. Thereafter, the pulse number and amplitude may be obtained from the same or other specimens of the same material and configuration, stress can be varied and pulses number and amplitude measured. The number and amplitude of pulses so obtained represent the stress in accordance with the calibration curve obtained from the known specimen.

In a typical situation, the specimen 12 may be in a larger structure and may be substantially obscured by its incorporation within the structure. Nevertheless, measurements can still be obtained even in the large structure. Once a calibration is compiled, the stress occuring in the specimen in the structure can be measured and observed by use of the present invention.

The method of the present invention is repeatable. The repeatability appears to be substantially unlimited in that the data appear to be a function of the stress present in the specimen, and there seems to be no change or variation merely from the passage of great amounts of time.

The present invention responds to an overall stress level in the magnetized region when only one acoustic sensor is used. Stress concentration within the specimen may occur for geometric or other reasons. Localized stress concentrations are not noted in and of themselves with a single sensor; rather, the stress in bulk is the factor which is observed. It is not possible, therefore, to specify the particular location or origin of the particular pulse when only one tranducer is used. With more than one sensor, however, it is possible to locate and verify by use of a multi-transducer array the location in the specimen of particular acoustic sounds. This enables greater definition to be obtained in mapping stress. For instance, stress may concentrate in a given locale, giving rise to spatial bias in the acoustic signals. By time contrasting the data at several sensors, the locale can be identified and confirmed from the data.

In addition to stress, the microstructure of a specimen also influences the Barhbausen pulses. This is because the number of magnetic domain wall shifts that occur in a given increment of magnetic field variation depends on the magnitudes of internal forces that tend to impede domain growth. These forces are associated with interactions between domain walls and dislocations, grain boundaries, particles, and other crystalline imperfections and, therefore, depend on the manner in which metal specimens are processed. As an example, forging, casting, heat treating, cold working and other metal working procedures modify the microstructure. Because the magnetic field strength at which each Barkhausen pulse occurs is directly proportional to the force that tends to restrict a change in the domain wall, it follows that the pulses will occur at different field strengths in materials with different distributions of crystalline defects. Thus, differences in microstructure can produce variations in both the amplitude and number of Barkhausen pulses. The fact that Barkhausen signals are sensitive to metallurgical parameters other than stress offers the potential of using Barkhausen measurements for microstructural characterization. This includes measurement of hardness, grain size and plastic deformation.

The same apparatus and methods described for stress measurements using the acoustic Barkhausen method may also be utilized for microstructure determination. In this application, the amplitude and number of acoustic Barkhausen pulses is dependent upon the particular microstructure of a specimen. For example, in certain materials, an increase in hardness results in a decrease in the maximum cumulative pulse count, and plastic deformation results in a redistribution of the number of pulses as a function of magnetic flux level in the specimen.

While the foregoing describes the preferred embodiment and method of the present invention, the scope is determined by the claims which follow.

We claim:

1. A method for testing a ferromagnetic specimen for stress levels therein which comprises the step of:
    (a) forming a magnetic field in the specimen;
    (b) varying the magnetic field from the first magnetic level to a second magnetic level to expose the specimen fully thereacross to a field which creates acoustic pulses fully thereacross;
    (c) placing an acoustic sensor in proximity of the specimen for observing individual acoustic pulses created within the specimen on movement of magnetic domain walls within the specimen with magnetic field change; and
    (d) tabulating the individual acoustic pulses created within the specimen as a measure of the stress within the specimen.

2. The method of claim 1 wherein the step of varying the magnetic field includes varying the magnetic field through zero flux to a selected magnetic level.

3. The method of claim 1 wherein the steps of varying the magnetic field includes varying the magnetic field from a negative level to a positive level passing through zero flux.

4. The method of claim 1 wherein the magnetic field is cyclicly varied from a first level to a second level.

5. The method of claim 1 wherein the step of tabulating the pulses observed from the specimen occurs during the interval in which the magnetic field is changed between the first and second levels.

6. The method of claim 5 wherein the pulses are counted and summed by a pulse counter means.

7. The method of claim 5 wherein the integral of pulse width and amplitude for all pulses is summed.

8. The method of claim 5 wherein the maximum amplitude of the pulses are tabulated.

9. The method of claim 6 wherein an analog signal is formed from the pulses during the change in magnetic level and the signal so measured is proportional to the pulses occurring in the specimen.

10. The method of claim 1 including the step of varying the magnetic field level maximum.

11. The method of claim 1 including the step of varying the rate at which the magnetic field is changed.

12. The method of claim 1 wherein the tabulating step includes summing the total of pulses observed by the acoustic sensor from a beginning time to an ending time during variation of the magnetic field to a total proportional to stress in the specimen.

13. The method of claim 12 including the step of totaling pulses of a specified pulse width and pulse height range in a pulse counter for a specified time interval.

14. The method of claim 1 wherein said field level change is from a lower to a higher level.

15. The method of claim 1 wherein said field level change is from a higher to a lower magnetic level.

16. The method of claim 1 wherein the tabulated value is indicated.

17. The method of claim 1 wherein the tabulated value is recorded.

18. Apparatus for measuring stress in a ferromagnetic specimen comprising:
    (a) magnetic field forming means forming a field characterized by a minimum and a maximum flux value and which means is adapted to form flux in a specimen fully thereacross;
    (b) acoustic vibration sensor means operatively coupled to the specimen to detect acoustic vibrations of a specified pulse width size on change of flux value and such acoustic vibrations are received fully thereacross;
    (c) amplifier means connected to said acoustic vibration sensor means for amplifying individual pulses representative of the acoustic vibrations; and (d) an indicating means connected to said amplifier means for measuring stress within the material, as a function of said amplified pulses.

19. The apparatus of claim 18 wherein said indicating means includes pulse summing and counting means connected to said amplifier means for summing and indicating the distribution of pulses occurring in the interval of time required for the field to change between minimum and maximum which sum and distribution is related to stress in the specimen.

20. The apparatus of claim 18 wherein said indicating means includes pulse amplitude measuring means for measuring pulse amplitudes occurring during the field change which amplitudes and distribution of amplitudes is related to stress in the specimen.

21. The apparatus of claim 18 wherein said acoustic vibration sensor means is connected to a band pass filter means.

22. The apparatus of claim 21 wherein said filter means is serially operative with said amplifier means to limit the input signal thereto.

23. The apparatus of claim 18 wherein said acoustic vibration sensor means is positioned against the specimen to form elecrical signals representative of acoustic vibrations and wherein said amplifier means amplifies signals therefrom.

24. The apparatus of claim 19 wherein said pulse summing and amplitude measuring means is a pulse counter and amplitude analyzer having an input from said amplifier means and wherein said pulse and amplitude analyzer is resettable to a beginning value.

25. The apparatus of claim 19 wherein said pulse summing and amplitude measuring means is a time base chart recorder.

26. The apparatus of claim 18 wherein said acoustic vibration sensor means is serially connected band pass filter means.

27. The apparatus of claim 18 including multiple acoustic vibration sensor means separately and selectively coupled to the specimen to form signals from spatially variant positions relative to the specimen.

28. The apparatus of claim 27 wherein each of said multiple sensor means forms outputs for an individual indicating means.

* * * * *